(12) United States Patent
Schaefer et al.

(10) Patent No.: US 7,544,210 B2
(45) Date of Patent: Jun. 9, 2009

(54) MEDIAL AND LATERAL FEMORAL IMPLANTS FOR SINGLE-COMPARTMENT KNEE PROSTHESIS

(76) Inventors: Roberto Schaefer, Juncal 2449 5° A, Ciudad de Buenos Aires (AR) 1425; Martin Jorge Morhac, Acassuso 1777, Provincia de Buenos Aires (AR) 1643

( * ) Notice: Subject to any disclaimer, the term of this patent is extended or adjusted under 35 U.S.C. 154(b) by 0 days.

(21) Appl. No.: 11/065,294

(22) Filed: Feb. 25, 2005

(65) Prior Publication Data

US 2005/0197709 A1    Sep. 8, 2005

(30) Foreign Application Priority Data

Feb. 27, 2004    (AR)    ............................... P040100619

(51) Int. Cl.
    *A61F 2/38*    (2006.01)
(52) U.S. Cl. .................................... 623/20.3
(58) Field of Classification Search ............... 623/20.3, 623/20.18, 20.31
    See application file for complete search history.

(56) References Cited

U.S. PATENT DOCUMENTS

| 3,816,855 | A | * | 6/1974 | Saleh | ..................... | 623/20.31 |
| 5,336,266 | A | * | 8/1994 | Caspari et al. | ........... | 623/20.35 |
| 7,115,131 | B2 | * | 10/2006 | Engh et al. | ..................... | 606/79 |
| 2006/0025865 | A1 | * | 2/2006 | Reich et al. | ............... | 623/20.35 |

* cited by examiner

*Primary Examiner*—Bruce E Snow
(74) *Attorney, Agent, or Firm*—James Creighton Wray; Meera P. Narasimhan

(57) ABSTRACT

A single-compartment knee prosthesis provides different femoral implants for the medial and lateral compartments. Both femoral implants feature distinct bends and slight twists following the anatomical shape of the corresponding compartment, of about 22° for the medial implant (11) and 14° for the lateral femoral implant (31). The complementary tibial plates also differ according to whether they are adapted to the medial or to the lateral compartment. In the latter case, the shape of the tibial plate (39) is substantially semicircular whereas the medial tibial plate (19) is more elongated.

3 Claims, 8 Drawing Sheets

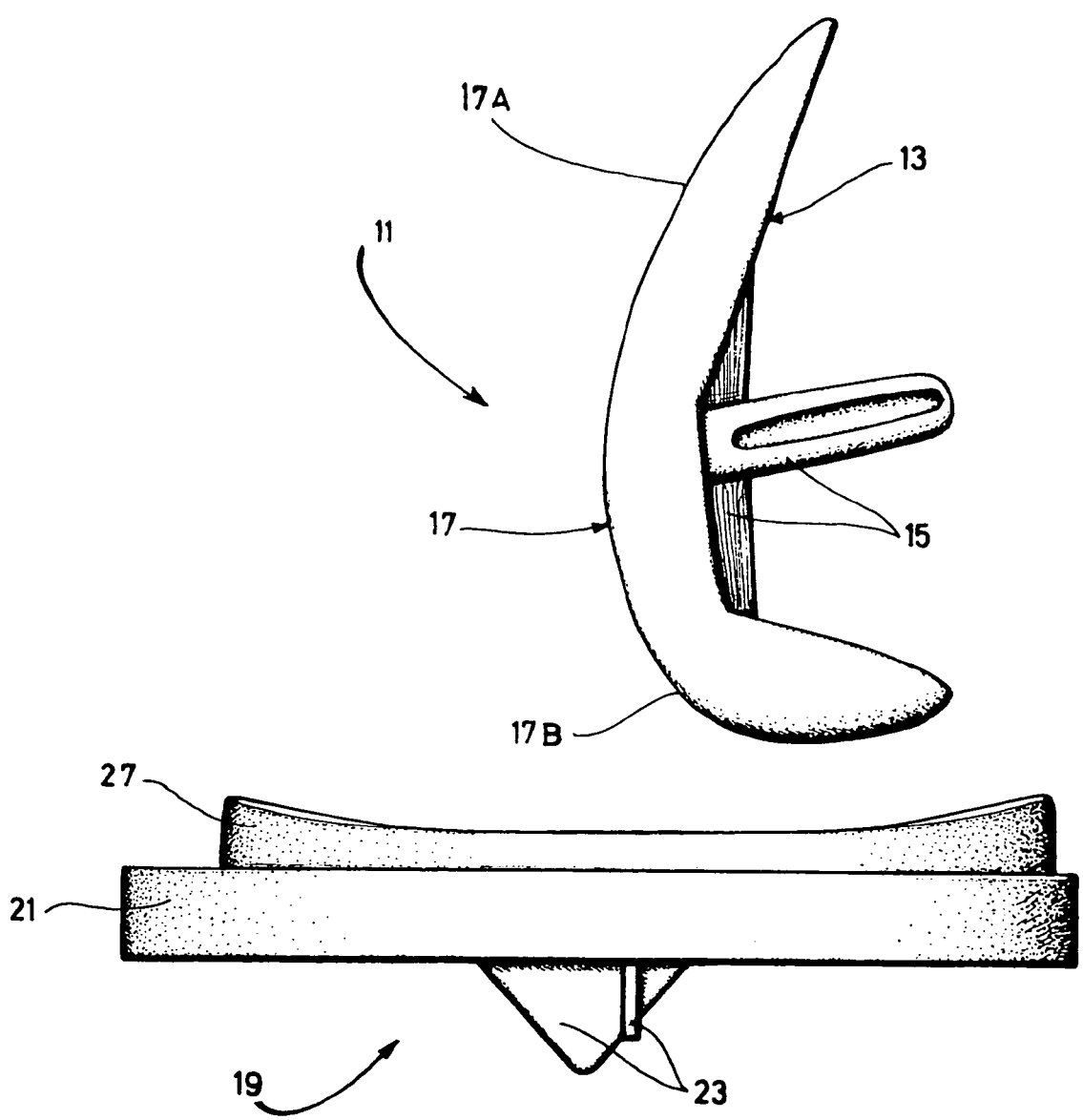

FIG. 10
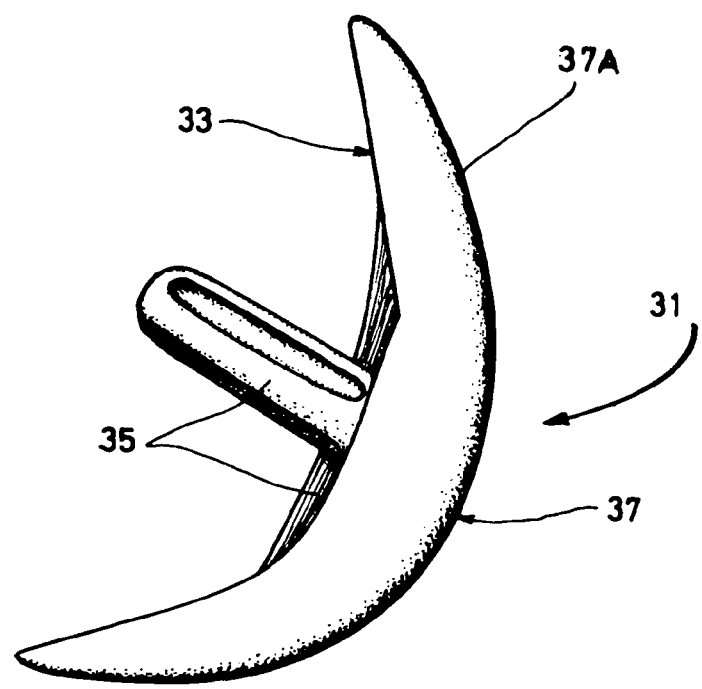
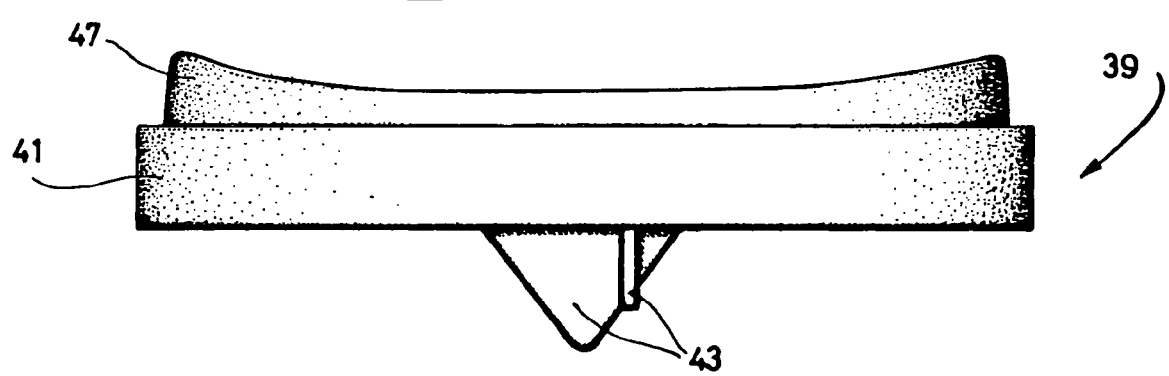
FIG. 14

MEDIAL AND LATERAL FEMORAL IMPLANTS FOR SINGLE-COMPARTMENT KNEE PROSTHESIS

This application claims the benefit of Argentine Application No. P20040100619 filed Feb. 27, 2004, which is hereby incorporated by reference in its entirety.

INDUSTRIAL APPLICATION AND FIELD OF THE INVENTION

This invention is related in general to orthopædia and arthroplastia; in particular to medial and lateral single-compartment knee prosthesis, as well as to femoral components thereof and tibial plates or implants for forming complete single-compartment prosthesis.

Such prosthesis are an important therapeutical option in medicine for rebuilding joints, specially in joints suffering medial or lateral unicompartimental arthrosis, as found in patients with a genu varo/arthrosic valgo or osteonecrosis, following tibial plate fractures.

BACKGROUND OF THE INVENTION

The knee joint essentially operates under compression under the effect of gravity. Its movement features a primary degree of freedom, which is flexoextension (normally in a 160° arch) and a secondary degree of freedom which is rotation about the longitudinal axis of the leg. The latter secondary rotation is present only when the knee is bent since, when the knee is extended, the tibia becomes locked against rotation with the femur. Some mechanical play in the joint allows extra lateral movement when the knee is slightly bent but this small degree of freedom disappears when the knee is fully stretched except in some pathological cases.

Since knees have to satisfy two diverse features, which are extensive mobility when bent more than a certain angle and high stability when straight and the knee has to support the body weight with long lever arms, it is vulnerable to articular fractures and other damage.

Flexoextension, which is the main degree of freedom of the knee, is conditioned by a joint of the troclear type because of the convex shape in both directions of the two (lateral and medial) femoral condyles. Hence, the knee is a dicondylear joint in anatomical terms and a specific troclear joint in mechanical terms.

On the tibial side, the surfaces are shaped conversely over dual parallel concavely landings, the glenoids, separated by a blunt anteroposterior crest where the tibial crown is located. The blunt crest fitting into the inter-condylear cleavage prevents axial rotation in extension.

From the functional point of view, the knee joint includes two joints, the femorotibial joint and the femoro-patelar joint. The former is formed by the condyles clasping onto their glenoids in a way such that the tibial crown fits into the intercondylean cleavage. The femoropatelar is formed by two slopes of the articular surface of the knee-cap with two faces of the femoral troclea, such that the vertical blunt crest couples into the troclear cleavage.

Just from the flexoextension point of view and in a first approach only, one may imagine the knee joint like a dicondylean knee surface sliding over dual matched concave landings. However, reality is quite more complex.

When the condyle and glenoid bearing surfaces are subject to excessive or uneven wear, the joint starts operating badly, the surrounding soft tissue may swell, the area becomes painful, knee movement becomes acutely restricted and so does the amount the knee is able to bend. As an alternative to replacing the entire knee by an orthopedic joint, unicompartimental knee surgery was suggested around 1970, consisting in replacing the bearing surfaces of the damaged compartment, either the medial (internal) compartment or the lateral (external) compartment, regardless of the other, or both. Aside from being surgically less invasive, this treatment sacrifices less healthy bone matter and retains the femoro-patelar joint and the ligament structure of the knee, in addition to the colateral compartment when it is in adequate anatomical and functional conditions.

SUMMARY OF THE PRIOR ART

U.S. Pat. No. 3,958,278 discloses an endoprosthesis adequate for uni- o dicondylean implants which may be replaced once it wears out. It uses like unicompartimental femoral components with a bicompartimental tibial plate.

U.S. Pat. No. 5,312,411 discloses a surgical instrument for machining condyles and drilling anchoring holes for unicondylar prosthesis. FIGS. 9 and 10 thereof show a prosthesis which may be implanted using this instrument.

EP patent publication No. 611,559 discloses a unicompartimental knee prosthesis.

U.S. patent publication No. 2002/0068979 discloses a femoral component for an orthopedic prosthesis.

In all the abovementioned prosthesis, the anteroposterior axis of the femoral implant is straight, generally perpendicular to the longitudinal axis of the femur; see FIG. 2 of U.S. Pat. No. 3,958,278, FIGS. 7 and 10 of U.S. Pat. No. 5,312,411, FIG. 1b of EP patent publication No. 611,559 and FIG. 8 of U.S. patent publication No. 2002/0068979.

In addition, in all known cases, like femoral implants are used in both the medial (internal) and in the lateral (external) positions, the only differentiation being a question of laterality, in other words the curvature in the cross-direction (i.e. inside-to-outside or left-right direction). That is, identical implants are used for the left leg medial femoral implant as for the right leg lateral implant, and viceversa. This exchangeability is made possible by the anteroposterior straightness of the femoral implants.

Presumably, the reason behind this straightness is not simply a desire for exchangeability but rather stems from a biomechanical conception of all these prosthesis. In other words, the joints are designed as mechanical models which copy the desired natural movements summarized hereinabove. Since the flexoextension movement is about a generally horizontal transverse joint axis, the conventional designs result in implants extending in vertical longitudinal planes, in which condyle-like convexities are situated.

Thus the movement of such an orthopædical knee is not completely natural, movements are somewhat restricted according to biomechanical models, thereby subjecting implants to wear. Implanted patients have to get accustomed to movements that feel different and generally experience some loss of comfort.

In effect, the shape of human condyles is rather complex. There is convexity both in the inside-to-outside direction of the knee and from back-to-front (anteroposterior direction). According to the well known Kapandji model shown in *Fisiología Articular*, chapter II, FIG. 42, the anteroposterior curvature varies both forward and rearward from a section which Kapandji calls the "T-point".

In addition to the inside-outside and the back-front convexities, each condyle further features a half-moonlike twist or bend about a vertical axis parallel to the longitudinal axis of the femur, as shown in Kapandji cit., FIG. 42. That is, the main movement of the condyles lacks fixed axes, rather the movement centres travels according to loci defined by the geometry of each condyle, as may be seen in FIGS. 45 and 46 in Kapandji cit.

Attempts to balance out this defficiency have included bearing such conventional femoral implants on mobile tibial implants. WO patent publication No. 02/09,623 discloses a medial lateral single-compartment knee prosthesis; more particularly a tibial implant featuring a polyethilene bearing plate for the femoral implant. The plate is mounted with an angularly-reduced degree of turning freedom in a horizontal plane (that is, generally transversal to the longitudinal axis of the tibia) over the base plate of the tibial implant which, in turn, features a typical plug arrangement, in this case comprising two pegs (one of which coincides with the pivot axis of the bearing plate), for anchoring to the tibia bone.

Single-compartment knee systems are known to be marketed by Zimmer, Inc., from the U.S.A., under an M/G designation. Its femoral components differ from the former in that they are not completely straight but feature a slight bend. However, their degrees of inclination and curvature radii are still inadequate since the design thereof privileges maintaining cross exchangeability of the femoral components (i.e., the left medial component with the external right one, and vice-versa). As a result, the values of the above-stated bend and curvature radius simply attempt to average out or minimize differences but in no way take into account the actual anatomical differences between the medial and lateral condyles.

The same can be said regarding the hemi-prosthesis femoral join element shown in FIGS. 1 and 4 of U.S. Pat. No. 5,871,541 (by Bruno Gerber, assigned to Plus Endoprothetik AG—Switzerland). Although the pictures show some degree of bend, the disclosure does not dwell on this feature and rough measurements on the paper show it to appear to be about 15°. Furthermore, this U.S. Pat. No. 5,871,541 cites German patent 2,550,704 (to National Research Development Corp.—UK) saying that the artificial endoprosthesis imitates the geometry of the "natural" knee joint and the bearing surfaces; however the drawings of the latter German patent depict straight femoral elements, suggesting away from a bend or a twist in a "naturally" shaped femoral implant element.

Lastly, U.S. Pat. No. 6,770,099 (to Zimmer Technology, Inc.—US) shows a total implant including femoral and lateral components, the posterior tips of which have distinct heights (A≠B) and curvature functions (R136≠R146) of the articulating surface.

SUMMARY OF THE INVENTION

The present invention stems from recognizing and Addressing operation deficiencies in current conventional prosthesis and in their biomechanical conception. As the cited Kapandji model teaches, nature has oriented the condyles in diverging directions and provided the glenoids with bearing surfaces lacking straight sections in any one of the tri-dimensional directions.

Therefore, an object of this invention a knee prosthesis based on an anatomical conception for copying complex human knee movements more naturally.

This and other objects and advantages are achieved in single-compartment medial/lateral knee prosthesis by means of a femoral component shaped such that the artificial condyle thereof is shaped with a bend and a twist such that the anterior face thereof is at an angle to the longitudinal axis of the condyle (which in turn is at an angle to the femur axis). That inclination angle being different depending on whether it is a medial or a lateral implant. In other words, the invention provides two distinct single-compartment femoral implants for the medial and lateral compartment, which further differ according to their laterality (i.e., axial symmetry), whether they are destined to the left or the right knee.

The term "twist" as used herein means that, in addition to the bend, the bearing surface forms a kind of slightly spiral landing portion such that the inclination of the surface sections changes along said portion, a small distance forward from Kapandji's "T-point", as may be observed in a real condyle. As a result, the present invention fundamentally provides for four distinct femoral implants which differ insofar their bend-and-twist direction and inclination, for the respective four different knee compartments found in the lower members of a human being.

The present invention further includes tibial plate implants for the prosthesis which are morphologically different depending on their medial or lateral position.

BRIEF DESCRIPTION OF THE DRAWINGS

These and other features, improvements and details of the object of this invention and the manner in which it may be reduced to practice may be understood better by means of the following detailed description, by way of example only but not to restrict the scope of the invention, of embodiments shown in the attached drawings, wherein:

FIG. 3 is a sagital view of the single-compartment medial femoral implant of FIGS. 1 and 2;

FIG. 7 is a sagital elevational view of the tibial Implant of FIGS. 5 and 6;

FIG. 10 is a sagital view of the femoral lateral implant of FIGS. 8 and 9;

FIG. 14 is a sagital elevational view of the tibial lateral implant of FIGS. 12 and 13;

DETAILED DESCRIPTION OF SOME EMBODIMENTS

Figure 1:
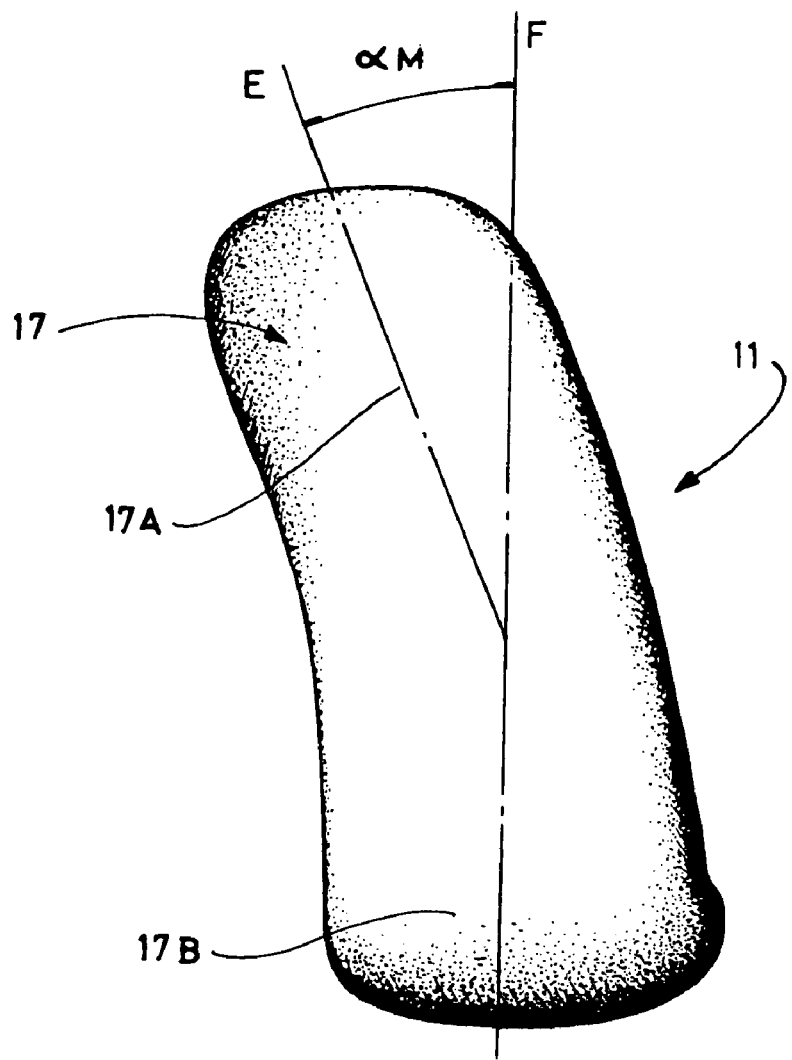
FIG. 1 is an anteroposterior view of a medial femoral implant for a single-compartment knee prosthesis according to this invention.
Figure 2:
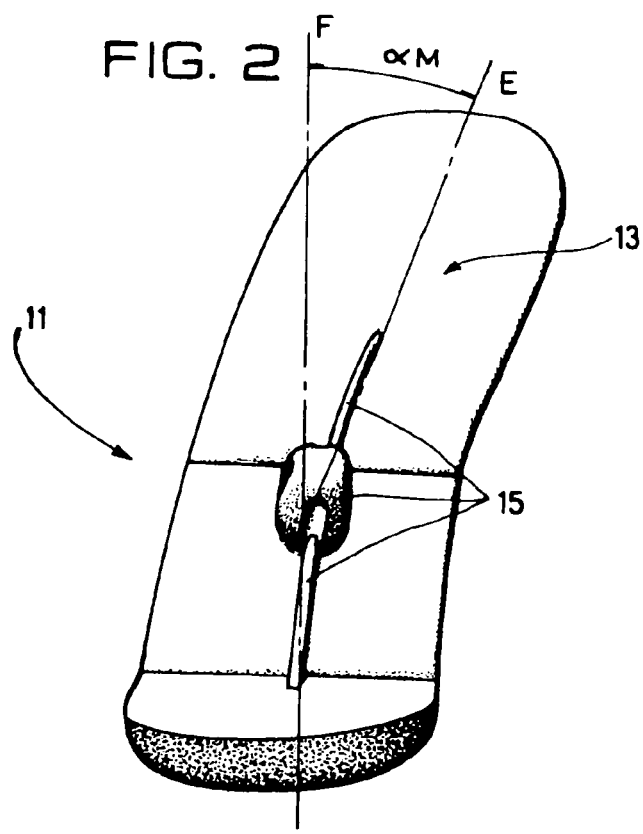
FIG. 2 is a rear view of the medial femoral implant of FIG. 1.

Describing in detail how the invention may be reduced to practise, the drawings depict the implants of the single-compartment knee medial-lateral prosthesis including the essential features of the present invention according to a preferred embodiment. FIGS. 1, 2 and 3 embody a femoral medial implant or implant 11 made from titanium or other suitable, preferably metallic material at least two 2 mm thick, not more than 16 to 18 mm across according to the size of the patient. Anchoring means 15 project from its inner side 13 for anchoring to the femoral bone of the patient to be implanted.

The anchorage means 15 may comprise a plug, peg or thorn and an antirotary crest (as illustrated) or alternatively two pegs as known in some conventional femoral implants such as the forementioned Zimmer's. The peg 15 is about 15 mm long and is inclined 30° from back to front and from distal to proximal.

The front face 17 forms a contact surface which is discretely convex, one part 17A of which bears on the tibial plate 19 (inter alia FIGS. 5-7) when the leg is stretched and another part 17B for bearing on the tibial plate 19 when bending the knee. The convexity in the left-right direction determines a curvature radius which is about 60% greater than the width of the implant 11 or, in other words, forms an arch subtending an angle of about 35-36°, i.e. about one-tenth of a circumference. For instance, for a typical width of 2 centimeters, the curvature radius of the transverse convexity is about 3.2 centimeters. The arch may be well-rounded to make the implant more tolerant or self-adjustable to slight installation variations or else be slightly flattened in the middle to conform more closely to anatomical morphology.

Figure 4:
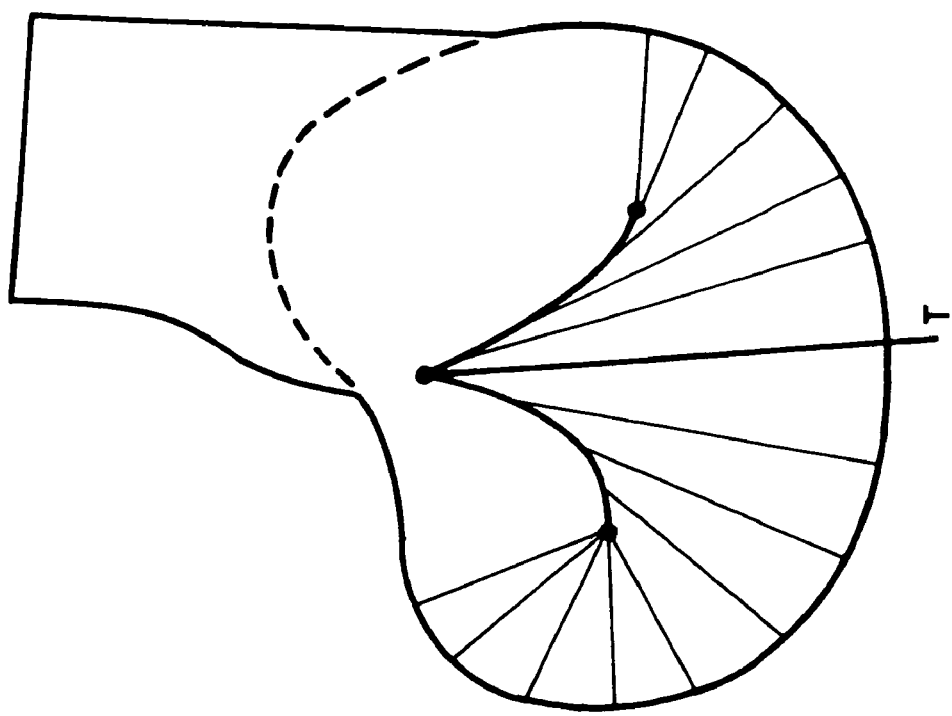
FIG. 4 is a schematic view representing the variation of the curvature radius of the medial femoral implant of FIG. 3.

FIG. 4 graphs the variation of the curvature radius of the "landing" of the artificial condyle, following the cited Kapandji model. The landing is shown as a condyle profile defined by the locus of the successive contact points that bear on the tibial plate during movement in a full range between complete flexion and extension. Of course, the so-called contact point is not really a point but a surface, the contact point being considered as the contact surface center-point or the point of maximum instantaneous bearing pressure transmission.

Referring back again to FIGS. 1-3, the contact surface 17 is shaped with a significant bend compounded with a slight twist when seen in anteroposterior view such that, when the knee is bent 90°, the surface 17A determines an inclination to the condyle axis of about 22°, say in the range of 19° or 20° to 30°. The condyle angle is given as the natural inclination of the condyle relative to the femur longitudinal axis, about 19° in the case of the medial condyle. In FIG. 1, the "twist" can be envisaged as the upper left corner pushing slightly into the page and the upper right corner conversely coming out of the drawing page towards the viewer, the degree of the resulting bend-plus-twist curve is indicated by the angle $\alpha_M$ between the condyle axis F and the projection on the drawing page of the contact tangent direction E in the extended position.

The side-view of FIG. 3 shows how the bend-and-twist of the femoral implant 11 follows the normal anatomy of the internal condyle, tracing a spiral or evolutive curve as described by Fick. The prosthesis 11 extends from the point of the condyle corresponding to the foremost one of the femorotibial bearing points (Kapandji's "T-point") to the rear region of the condyle. The rear part 13 comprises several flat faces, as suggested by Zimmer et al, for facilitating and standardizing the surgical machining down of the condyle bone for preparing it to receive the implant.

Figure 6:
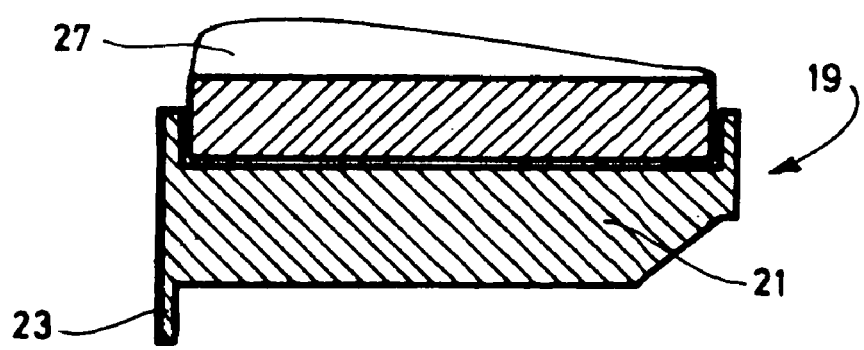
FIG. 6 is a cross-sectional view of the tibial medial implant of FIG. 5.
Figure 5:
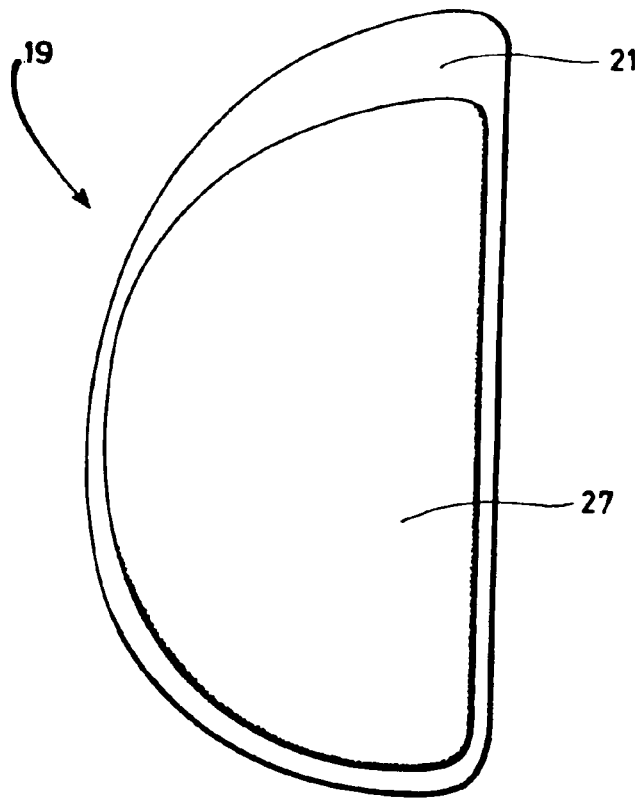
FIG. 5 is a top plan view of a medial tibial implant matching the femoral implant of FIGS. 1, 2 and 3 with which it may form a single-compartment medial knee prosthesis according to this invention.

The tibial medial implant 19 is illustrated on its own in FIGS. 5, 6 and 7. It comprises a metallic base 21 made of titanium, a chrome and cobalt alloy or suitable material 2 mm thick for instance. Its underface features a rough surface and two perpendicular crests 23, one in the shape of a wedge and the other as a blade, for anchoring to the tibia of the patient, affixing the implant 21 against play and relative movement of any kind, including rotation and slipping on the surface of the tibia.

At its upper face, the base 21 features a depression 25 for receiving a snap-in, polyethylene pad 27. The pad 27 is elongated in the anteroposterior (front-to-back) direction. Its topface is flat in the middle for the condyle to travel thereon and is smoothly ridged upwards about 2 mm at the front and back.

Figures 8, 13:
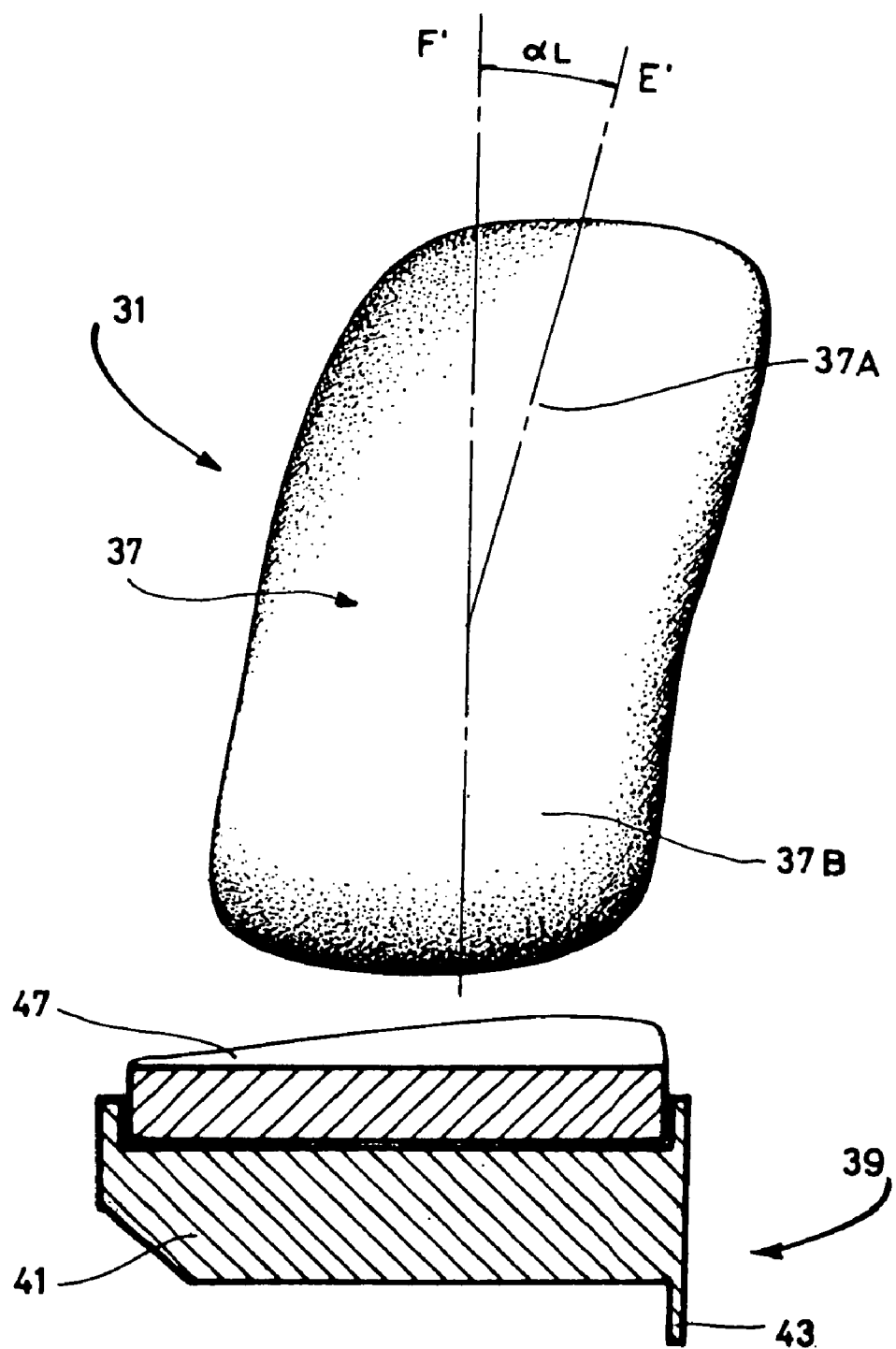
FIG. 8 is an anteroposterior view of a femoral lateral implant for a single-compartment knee prosthesis according to the invention.
FIG. 13 is a cross-sectional view of the tibial lateral implant of FIG. 12.
Figure 9:
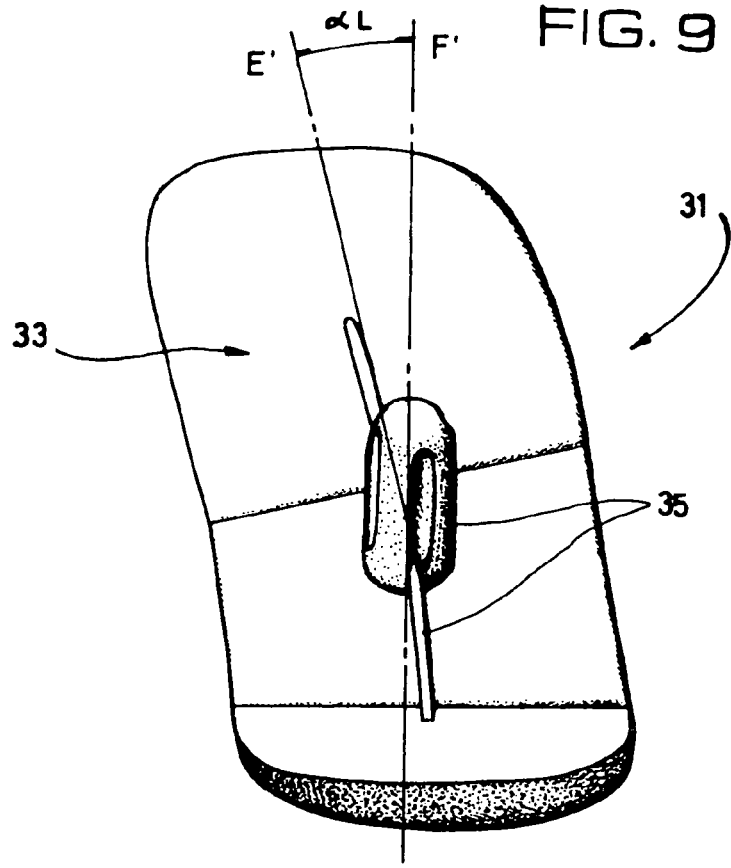
FIG. 9 is a rear view of the femoral lateral implant of FIG. 8.

FIGS. 8, 9 and 10 show an embodiment of the femoral lateral component or implant 31 which comprises a metallic member 33 (e.g. titanium) 2 mm thick not more than 16 to 18 mm across according to the size of the patient. Means 35 project from its inner side 33 for anchoring to the femoral bone of the patient in a similar way to that described in connection with the femoral medial implant 11. The front face 37 forms a contact surface which is discretely convex, one part 37A of which bears on the tibial plate 39 (FIGS. 12-14) when the leg is straight and another part 37B which bears on the tibial plate 39 while the knee is bent.

Figure 11:
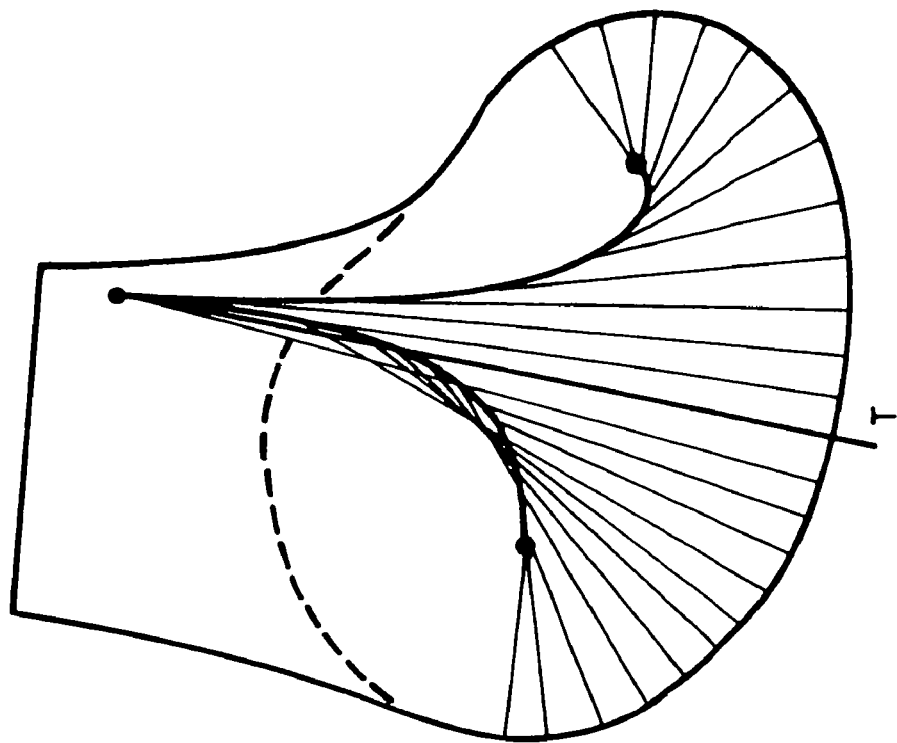
FIG. 11 is a schematic representing the different curvature radii of the femoral lateral implant of FIGS. 8, 9 and 10.

As before, the contact surface 37 is bent and twisted in anteroposterior view such that the anterior bearing surface 37A is at an angle $\alpha_L$ of about 14°, e.g. in the range of 10° to 17°, to the condyle axis. FIG. 11 graphs the progression of the curvature radius of the "landing" of the artificial condyle, following the cited Kapandji model for the lateral condyle.

As a result, both femoral implants 11 and 31 feature different bends, according to whether each corresponds to the medial or lateral position of the knee, which is greater in the medial implant 11 than in the lateral implant 31. There are also specific differences which the present invention does not neglect in their inclinations (angulations) and in the curvature radii. We have discovered that carefully copying the anatomic geometry or profile of these implants 11 and 31 provides a more natural movement of the knee, reduces the difficulties a patient may face until he or she assimilates the orthopedic movements and lengthens the useful lifeterm of the prosthesis. We have further found that these advantages easily compensate having to make specific femoral implants 11 and 31 available for each one of the four compartments.

The bend and the curvature of the implant 31 are distinct in that they closely resemble the normal anatomy of the external condyle, following the spiral or evolutive curve described by Fick. The prosthesis 11 extends from the point of the condyle corresponding to the foremost femoro-tibial bearing point (or Kapandji's "T-point") to the rear region of the condyle.

Figure 15:
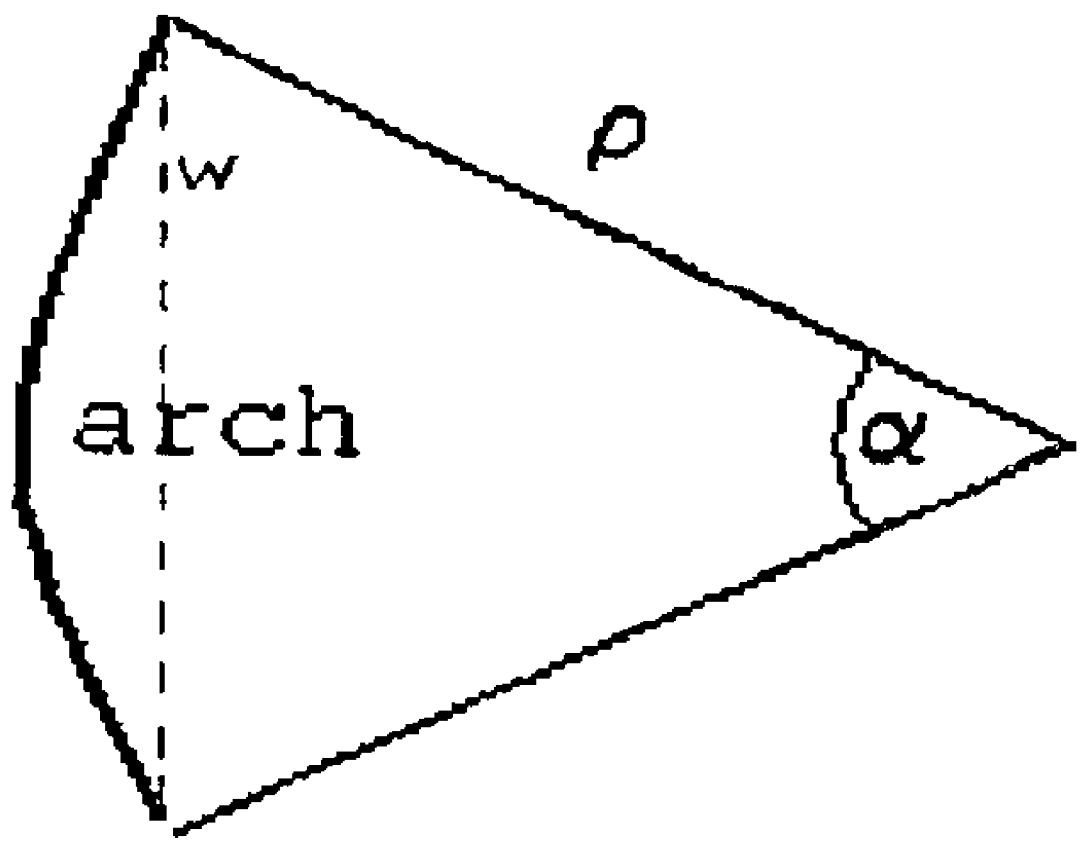
FIG. 15 illustrates the convexity of the implant in the left-right direction.

The convexity of the implant in the left-right direction is illustrated in FIG. 15. As can be seen in, for example, FIG. 3, the implant has a convex curvature or arch in the left-right direction. The curvature radius ($\rho$) of the arch is 60% greater than the width of the implant (w). The arch subtends an angle ($\alpha$) of about 35-36°.

Figure 12:
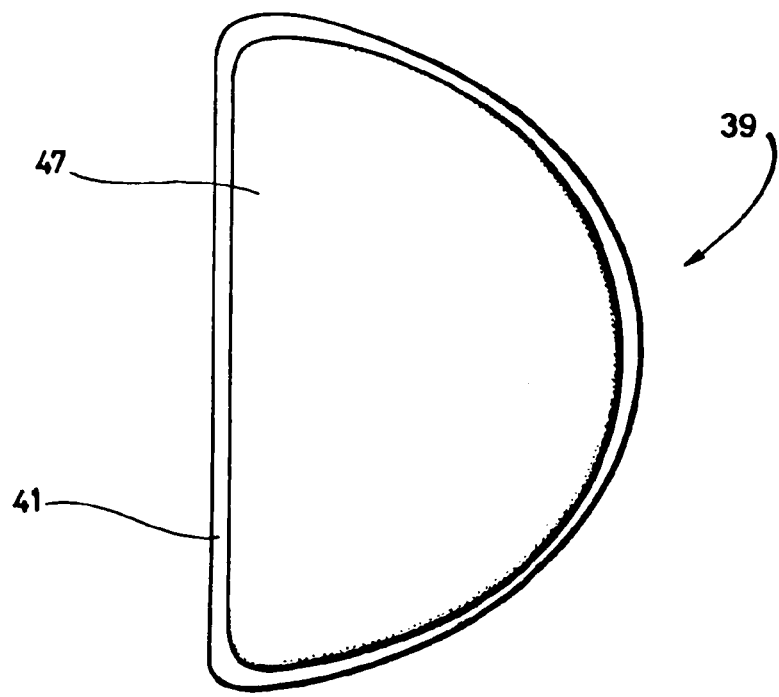
FIG. 12 is a top plan view of a tibial lateral implant matching the femoral lateral implant of FIGS. 8, 9 and 10 with which it forms a single-compartment knee lateral prosthesis according to this invention.

The lateral tibial implant 39 is illustrated in FIGS. 12, 13 and 14. Like the implant 19, it comprises a metal base 41 about 2 mm thick, the underface of which features a rough surface and two perpendicular crests 43 for good anchoring to the tibia of the patient, whereas its topface features a depression 45 for snapping a polyethylene plate 47 in. However, in contradistinction to the tibial medial implant 19, both the pad 47 and its metal base 41 are semicircular. The topface is generally flat and is smaller so as to allow less sliding thereon.

Of course, certain changes in the construction, materials, arrangement and shape of the detailed examples of the implants are foreseeable out without departing from the scope of the present invention. Dimensions of the implants may vary according to the size of each patient. In particular, the invention preferably foresees manufacturing the femoral implants 11 and 31 in six different sizes and the tibial implants 19 and 39 in five different sizes. The tibial plates may also feature different shapes, even flat shaped bearing surfaces are foreseeable.

The invention claimed is:

1. A single-compartment lateral knee prosthesis characterised by comprising:
    a lateral femoral implant for a single-compartment prosthesis of a knee, the femoral implant comprising a bearing surface for replacing that of the condyle of the corresponding medial or lateral knee compartment and an anchoring system for implanting the femoral implant to the femur of a patient in one of the corresponding medial or lateral knee compartments, wherein said bearing surface is provided with a shape closely following the anatomy of a normal condyle, and further that the bearing surface includes a predetermined bend with a twist in anteroposterior view and which is specific to the corresponding medial or lateral compartment of the knee, wherein said bearing surface includes an extension bearing portion bearing on a tibial plate at knee extension, said extension bearing portion having an inclination in the range of 10° to 17° to the lateral condyle axis, and
    a lateral tibial implant for bearing of a bearing member of said lateral femoral implant, said lateral tibial implant having a bearing surface closely shaped to the normal anatomy of the corresponding lateral glenoid, wherein the underface of the tibial implant(s) has a rough surface and two anchoring crests perpendicular to one another.

2. A prosthesis according to claim 1, wherein the topface of the tibial implant has a depression in which a plate of synthetic material snaps into.

3. A prosthesis according to claim 1, wherein said tibial implant is substantially flat in the cross-direction.

* * * * *